United States Patent [19]

Letson, Sr.

[11] Patent Number: 4,884,561

[45] Date of Patent: Dec. 5, 1989

[54] ARTICULATED BRACE FOR PROTECTION OF THE JOINT OF A WEARER'S LIMBS

[76] Inventor: Billy R. Letson, Sr., Rte. 2, Box 533, Trinity, Ala. 35673

[21] Appl. No.: 55,949

[22] Filed: Jun. 1, 1987

[51] Int. Cl.$^4$ .............................................. A61F 5/00
[52] U.S. Cl. ........................................ 128/77; 2/16; 2/24; 128/80 C; 128/88; 128/165
[58] Field of Search ............ 128/77, 165, 80 C, 80 R, 128/88, 80 F; 2/22, 16, 24

[56] References Cited

U.S. PATENT DOCUMENTS

| | | | |
|---|---|---|---|
| 3,898,697 | 8/1975 | Whitehead | 2/22 |
| 4,409,689 | 10/1983 | Buring et al. | 2/22 |
| 4,490,855 | 1/1985 | Figgie, III et al. | 2/24 |
| 4,599,748 | 7/1986 | Garcia | 2/22 |
| 4,617,920 | 10/1986 | Carsalade | 2/22 X |

Primary Examiner—Paul T. Sewell
Assistant Examiner—Moshe I. Cohen
Attorney, Agent, or Firm—C. A. Phillips

[57] ABSTRACT

A brace for protection and support of the joint of a wearer's limbs. The brace may be worn during periods of recuperation from injuries to the joint while also permitting the wearer to engage in contact sports, such as football, etc., while recuperating from such injuries.

14 Claims, 2 Drawing Sheets

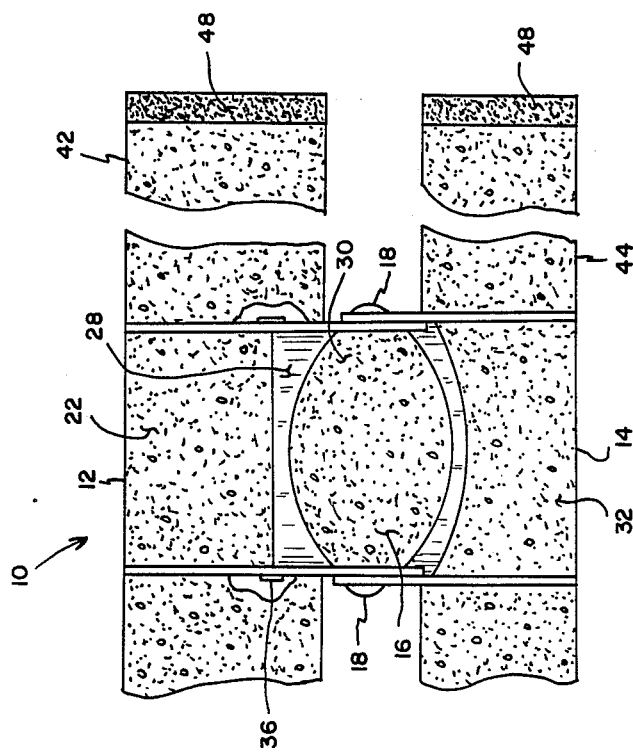
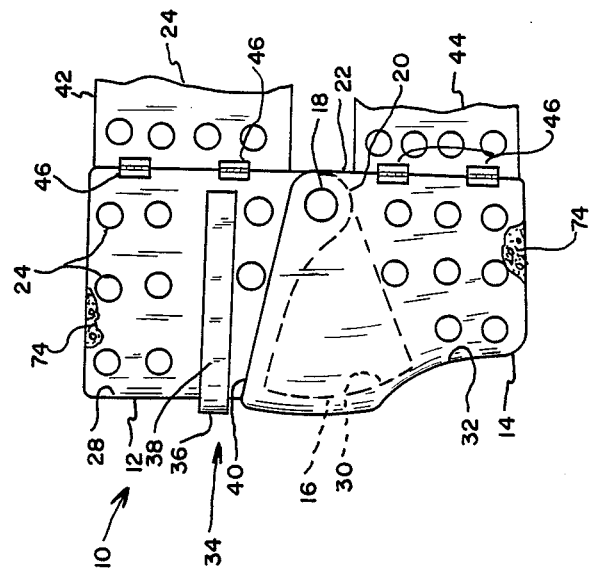

ARTICULATED BRACE FOR PROTECTION OF THE JOINT OF A WEARER'S LIMBS

FIELD OF THE INVENTION

This invention relates generally to a brace for protection and support of a joint of an individual's limbs, such as the elbow of knee joints. More particularly, this invention relates to such a device which will protect and support the joint while allowing substantially unencumbered movement thereof.

BACKGROUND OF THE INVENTION

Conventional braces which are utilized to support the joint of a wearer's limb normally provide support to the limbs in an area adjacent the joint and not to the joint itself. Specifically, in conventional knee braces, for example, the areas of the upper and lower leg which are adjacent the knee joint are generally supported by arcuate-shaped members which engage the upper and lower sections of the leg in pivotal relation to permit movement of these protective leg portions while the leg is pivoted. Such protective devices are shown in U.S. Pat. Nos. 1,186,043, issued June 16, 1916; 2,959,168, issued May 8, 1957; 3,898,697, issued Aug. 12, 1975; 4,139,002, issued Feb. 13, 1979; 4,409,689, issued Oct. 18, 1983; 4,599,748, issued July 15, 1986; and 4,633,529, issued Jan. 6, 1987. None of these references disclose a brace in which the joint itselt is protected and directly supported by a movable member which moves with the joint and remains in supporting mating relation with the joint even during rigorous movement thereof.

A feature of the present invention is its ability to protect a joint, such as an elbow or knee of a wearer, even when the wearer is engaged in strenuous activites, such as playing football, soccer, etc., while permitting relatively unencumbered movement of the limbs during such activites.

Additionally, the brace of the present invention is well suited for wearing by an individual during a period of recuperation from injuries to the joints and is beneficial in aiding an individual to more rapidly recover from such injuries than would otherwise be required.

SUMMARY OF THE INVENTION

A brace for protection and support of the joint of a wearer's limbs. The brace may be worn during periods of recuperation from injuries to the joint while also permitting the wearer to engage in strenuous activites, such as a game of football. The brace includes upper and lower arcuate sections for attachment to the limbs of a wearer adjacent to the joint of the limbs. An intermediate joint engaging "floating" section is provided in contiguous with the joint for directly contacting and supporting the joint even when the joint is impacted by an object. The sections are pivoted together for relative movement therebetween.

BRIEF DESCRIPTION OF THE DRAWINGS

FIG. 1 is a side elevational view of the brace of the present invention in its extended straight position.

FIG. 2 is a rear elevational view of the brace of the invention as shown in FIG. 1.

DESCRIPTION OF THE PREFERRED EMBODIMENT

Figure 3:
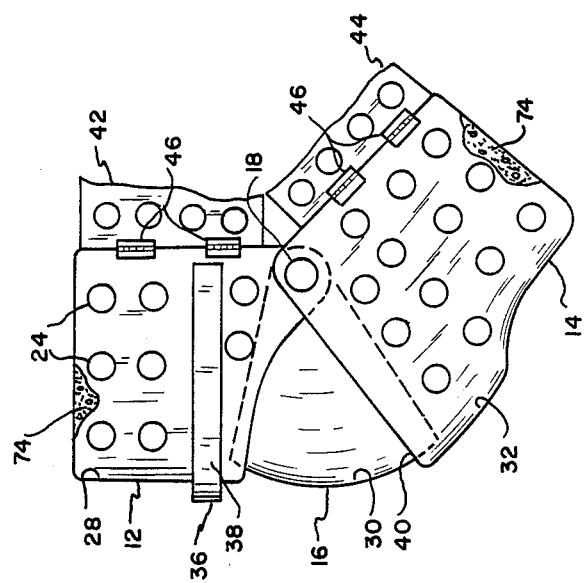
FIG. 3 is a side elevational view showing the brace bent as if following the configuration of a bent joint, such as a knee or elbow.

As seen in FIGS. 1-3, a brace 10 for use by an individual includes an upper arcuate section 12, a lower arcuate section 14, and an intermediate cupped section 16. Upper section 12 is disposed for attachment to an upper limb of an arm or leg of an individual, and lower section 14 is disposed for attachment to the lower limb of the arm or leg, while the intermediate section 16 is disposed inside of sections 12 and 14 for mating engagement with the joint, such as the elbow or knee cap, of the individual. The members are pivotally connected by a pivot connection 18 to permit relative movement therebetween. The pivot connection extends through a lower extending ear 20 of upper section 12 and through an upper portion 22 of the lower section 14.

As can be seen in FIGS. 1-3, the intermediate section 16 is mounted inside of the upper and lower members in "floating" nestled relation therewith. Such construction permits the intermediate section to move with the joint (elbow or knee cap) while supporting and protecting the joint even during movement of the joint in such activities as walking, running, or playing football, soccer, etc.

To provide ventilation to the limbs, a series of holes 24 is bored through the surface members of the brace.

To provide for comfort while the brace is worn, a padding material 22 is secured to the inner surfaces 28, 30, and 32 of the upper, intermediate, and lower sections, respectively.

To limit the pivotal movement of the brace in a direction that would allow for hyperextention of the limbs, a stop 34 in the form of a projecting ridge 36 (FIG. 1) is disposed at the lower portion 38 of upper section 12 for engagement with the uppermost surface 40 of lower section 14. It is to be understood that while ridge 36 is illustrated as being on the upper section, it could be on the lower section if the lower section were postioned on the inside of the upper section for pivotal movement inside the upper section.

As seen in FIGS. 1 and 3, a fastening device is secured to the upper and lower sections. The fastening device is shown to include membes 42 and 44 secured to upper section 12 and lower section 14 by hinges 46. If desired, the fastening device may be made of the same hardened plastic material so as the brace and padded and ventilated in similar manner. A strip of Velco ™ 48 (FIG. 3) may be provided on the distal ends of the fastening members to secure the brace to the limbs of the wearer. It is to be understood that any of many other fastening devices may be used if desired. For example, adjustable straps and buckles may be provided on the ends of the fastening members instead of Velcro ™.

Figure 5:
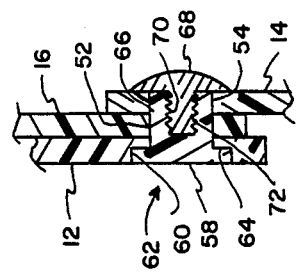
FIG. 5 is a view similar to FIG. 4 showing yet another means for pivotally securing the brace sections together.
Figure 4:
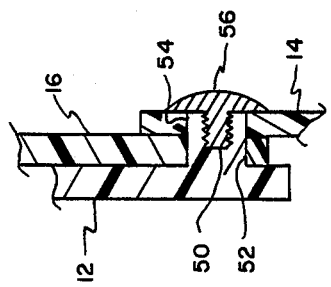
FIG. 4 is a sectional view through the pivotal connection of the brace of the present invention and illustrating a means for pivotally securing the brace sections together.

The device for securing the members in pivotal relation is shown in FIGS. 4 and 5. As seen in FIG. 4, upper section 12 is provided with a molded hollow shaft 50 extending therefrom. The shaft 50 extends through an opening 52 in intermediate section 16 and through an opening 54 in lower section 14. A cap member 56 includes a shank which may be pressed into the opening of the shank or threaded therein.

FIG. 5 illustrates a securing assembly including a member 58 having a cap 60 on one end 62 thereof which fits into a groove 64 on upper section 12. A hollow shank 66 extends from cap 60 through opening 52 of intermediate section 16 and through opening 54 of lower section 14. A second cap member 68 is provided with a shank 70 which is pressed or threaded into opening 72 of shank 70.

Typically the brace is made of ¼" plastic with spaced ¼" diameter breather holes and with approximately ¼" thick padding secured to the inside surface. Clearance between the knee cap section and the upper and lower sections is approximately 1/16" to permit swivel movement. The stop extends from the exterior surface approximately ¼". Padding may be provided on the exterior surface of the brace if necessary. The external padding may be approximately ⅜", or of any thickness required. External padding 74 is generally illustrated in FIG. 1.

It should be seen that applicant has provided an improved brace which may be worn by an individual while recuperating from injuries to the joint of the limbs. Additionally, it can be seen that applicant's brace permits movement of the joint while being worn by an individual and while also protecting the joint from further injuries as a result of impact. It is to be understood that applicant's brace may be tailor made for the particular size and configuration of the wearer or may be a shelf item which may be selected to match the size and configuration of the user.

What is claimed is:

1. An articulated brace having a pivotally mounted joint engaging portion for protection of the joint of a wearer's limbs, such as a knee or elbow, and comprising:

an upper, arcuate, shell-like section for attachment to the upper portion of a wearer's limb;

a lower, arcuate, shell-like portion for attachment to the lower portion of a wearer's limb;

an intermediate cupped section pivotally secured to and mounted inside said arcuate upper and lower sections in nestled relation therewith, said intermediate cup-shaped section disposed in contiguous relation with the joint of said wearer's limb even during movement thereof;

pivotally securing means for pivotally securing said upper, lower, and intermediate sections together, whereby said intermediate section retains the joint of said wearer's limb therein in nestled relation even during movement of said joint; and stop means for limiting the movement of said upper, lower, and intermediate sections.

2. A brace as set forth in claim 1 includin securing means for securing said upper, intermediate, and lower sections together in the pivotal relationship.

3. A brace as set forth in claim 2 including fastening means for fastening said brace to the limbs of the wearer.

4. A brace as set forth in claim 3 wherein the limbs of the wearer are the upper arms and forearms of the wearer, and said joint is the elbow joint, said fastening means being members extending from said upper and lower section of said brace for securely engaging the upper and forearm limbs of the wearer for secured relation of said brace to said upper arms and forearms.

5. A brace as set forth in claim 3 wherein the limbs of the wearer are the upper and lower section of the legs of the wearer, and said joint is the knee cap, said fastening means being members extending from said upper and lower section of said brace for securely engaging the upper and lower sections of the legs of the wearer for secured relation of said brace on said leg.

6. A brace as set forth in claim 3 including padding means secured on the inner surface of said upper, intermediate, and lower sections of said brace.

7. A brace as set forth in claim 6 wherein said brace is provided with spaced ventilation holes through the surface thereof.

8. A brace as set forth in claim 7 wherein said brace is made of hardened plastic.

9. A brace as set forth in claim 3 wherein said fastening means includes a first and second pair of members pivotally secured to said upper and lower sections, respectively, of said brace, each of the members of said pair of members being pivotally secured to opposite sides of said arcuate members and disposed for pivotal movement for mating engagement therebetween, and releasable attaching means secured to the mating surfaces to retain the mating surfaces in engagement for retention of said brace on the limbs of said wearer.

10. A brace as set forth in claim 9 wherein said releasable attaching means is a strip of Velco TM secured to said mating sufaces.

11. A brace as set forth in claim 3 wherein said securing means includes a pin extending through said upper, intermediate, and lower sections of said brace, and means for securing said pin in said sections for relative movement therebetween.

12. A brace as set forth in claim 11 wherein said pin is secured to said intermediate section and extends through a lower portion of said upper section and through an upper portion of said lower section, said pin having a central opening therein, said means for securing said in in said sections includes a member having a rounded cap portion disposed in engagement with the outer surface of said lower section and an extending shank portion disposed for snug fitting engagement in said central opening of said pin.

13. A brace as set forth in claim 3 wherein said upper member includes a lower portion having a projecting suface extending therefrom defining said stop means, said lower member having an upper surface disposed for engagement with said projecting surface to limit movement of said upper and lower members and thus prevent hyperextension of the limbs of the wearer.

14. A brace as set forth in claim 3 including padding means secured on the external surface of said brace.

* * * * *